United States Patent
Lebski et al.

(10) Patent No.: US 6,453,759 B1
(45) Date of Patent: Sep. 24, 2002

(54) APPARATUS FOR AND METHOD OF TAKING A PREDETERMINABLE VOLUME OF A SAMPLE OF MEDIUM

(76) Inventors: Hubert Lebski, Bayerstetten 14, 87484 Nesselwang (DE); Dieter Waldhauser, Akosweg 16, 87435 Kempten (DE); Wilhelm Schneider, Vorderegger Weg 4, 87629 Füssen (DE); Helmut Einsiedler, Falkensteinstrasse 4, 87629 Füssen (DE)

(*) Notice: Subject to any disclaimer, the term of this patent is extended or adjusted under 35 U.S.C. 154(b) by 0 days.

(21) Appl. No.: 09/362,178

(22) Filed: Jul. 27, 1999

(30) Foreign Application Priority Data

Aug. 1, 1998 (EP) .............................. 98114452

(51) Int. Cl.$^7$ ................................ G01N 1/14
(52) U.S. Cl. .................. 73/864.34; 73/863.01; 73/863.02
(58) Field of Search ............ 73/863.01, 863.02, 73/863.81, 864.34, 864.35

(56) References Cited

U.S. PATENT DOCUMENTS

| | | | |
|---|---|---|---|
| 3,587,670 A | * 6/1971 | Brailsford | 141/35 |
| 3,795,347 A | 3/1974 | Singer | 222/21 |
| 3,880,011 A | 4/1975 | Johnson | 73/421 B |
| 3,901,084 A | * 8/1975 | Brailsford | 73/421 B |
| 3,901,087 A | * 8/1975 | Fabritius | 73/421 B |
| 4,022,059 A | 5/1977 | Schontzler et al. | 73/198 |
| 4,037,472 A | 7/1977 | Gates | 73/421 B |
| 4,077,263 A | 3/1978 | Brailsford | 73/421 B |
| 4,083,252 A | * 4/1978 | Stookey | 73/421 B |
| 4,418,581 A | 12/1983 | Jones | 73/864.34 |
| 4,660,422 A | * 4/1987 | Eads et al. | 73/863.02 |
| 5,576,503 A | * 11/1996 | Nabity et al. | 73/863.01 |
| 5,796,015 A | 8/1998 | Dangelmaier et al. | 73/863.56 |

FOREIGN PATENT DOCUMENTS

DE 2824155 12/1979

* cited by examiner

Primary Examiner—Hezron Williams
Assistant Examiner—Charles D. Garber
(74) Attorney, Agent, or Firm—Bose McKinney & Evans LLP

(57) ABSTRACT

The apparatus makes it possible to change a desired sample volume—even during operation—in a simple manner without mechanical intervention, with any accumulation solids of a sample contained in a sample collecting vessel being avoided, so that a sample representative of the medium is obtained.

The apparatus comprises a control unit which controls a pneumatic control gear and switches a pump by means of which the medium is drawn into a sample collecting vessel via a hose or tube used as a suction line. A detection unit incorporated in the suction line signals the presence of the medium to the control unit, which then controls the time period for taking the desired volume of the sample. The sample volume obtained is drained off into a sample container via a drain device.

10 Claims, 1 Drawing Sheet

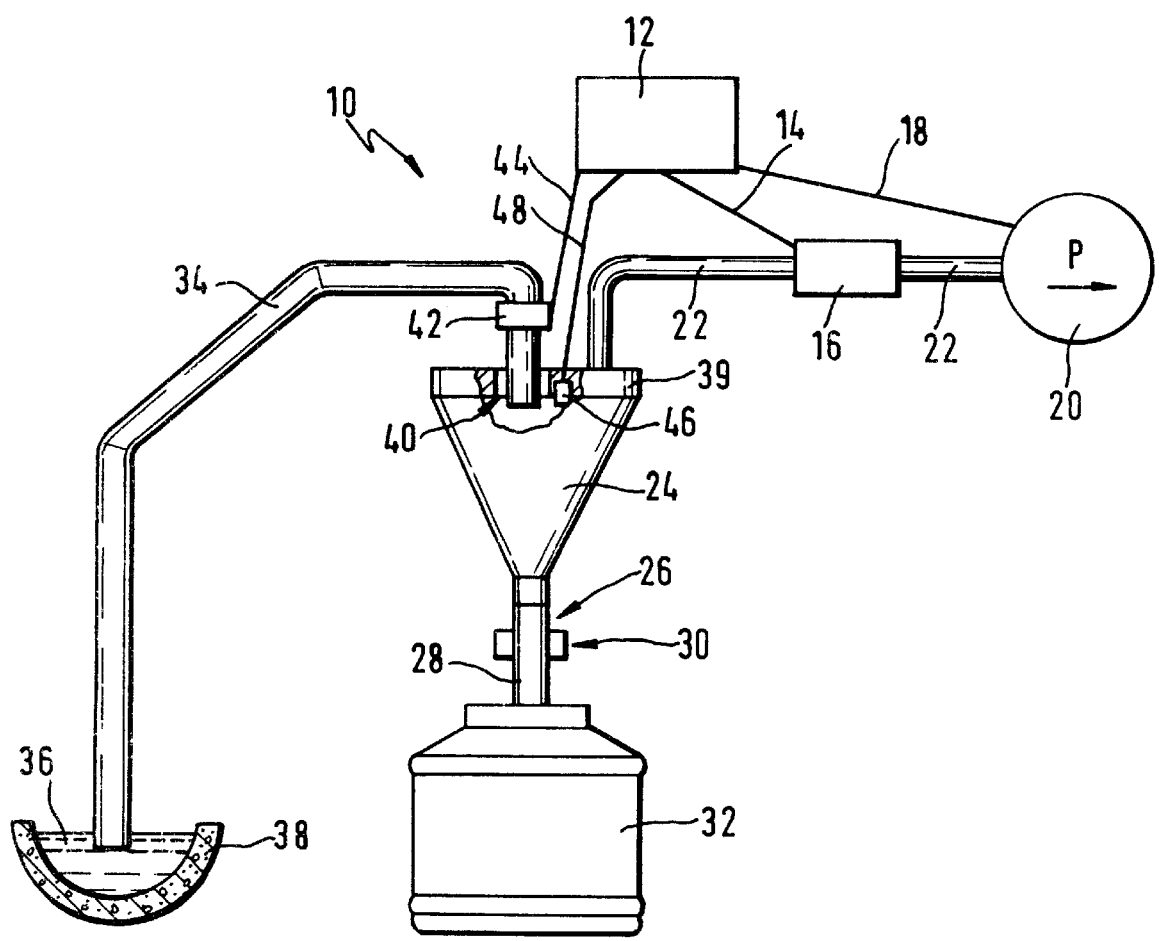

APPARATUS FOR AND METHOD OF TAKING A PREDETERMINABLE VOLUME OF A SAMPLE OF MEDIUM

This invention relates to an apparatus for and a method of taking a predeterminable volume of a sample of a medium. In particular, the invention deals with an apparatus and a method whereby a sample is taken from a medium flowing in an open channel or flowing by gravity through a pipe.

The medium (frequently one with a high solids content) is commonly drawn from the open channel or pipe by means of a pump over a suction line, generally a hose or tube, and conducted from above into a vertically mounted dosing vessel. The portion of the suction line which extends into the dosing vessel and is commonly referred to as a "dosing tube" has on its surface a scale in the form of marks with the aid of which a user can adjust that volume in the dosing vessel which is below the dosing tube in the dosing vessel and corresponds to the selected sample volume.

In a conventional sampling operation, the medium is drawn into the dosing vessel until the rising level of the medium reaches a sensor mounted in the upper part of the dosing vessel, i.e., until the dosing vessel is filled up. The sensor triggers a signal whereby the drawing in of the medium is stopped. Next, the dosing vessel is either pressurized or opened to the atmosphere in order to dose the desired sample volume. The quantity of the volume in which the dosing tube is immersed flows out of the dosing vessel, so that only the desired sample volume remains in the dosing vessel. In addition, the fluid contained in the suction line flows back into the open channel. The sample is then drained from the dosing vessel into one or more sample containers.

In the samplers described, the desired sample volume is adjusted only mechanically via the length of the dosing tube extending into the dosing vessel, namely by changing (generally permanently) the length of the dosing tube which is guided in a lid of the dosing vessel.

In another apparatus, described in CA-A-2,192,149, the length of the dosing tube in the dosing vessel can be changed by rotating the dosing tube, but this method, too, necessitates human intervention.

In conventional apparatus, the desired sample volume can generally be adjusted only when the apparatus is first put into operation or when the sample volume is changed. Changing the volume from one sampling operation to the next as an adaptation to a changing flow rate of the medium in the channel, as is desired, for example, for taking a sample volume proportional to flow rate, is not possible during continuous operation.

Another problem encountered with the sampling systems explained is that initially, more medium is drawn into the dosing vessel than is needed for the sample proper. As the dosing vessel is being filled, the solids of solids-containing media begin to sediment and accumulate in the lower portion of the dosing vessel, from which the sample is ultimately drained into a sample container.

When the excess medium flows out of the dosing vessel (upward) back into the channel, the sedimented solids of the excess medium, too, will remain in the lower part of the dosing vessel. Due to the sedimentation, however, the concentration of the solids in the sample in the lower part of the dosing vessel has already increased to the point that the sample to be drained off into a sample container is no longer representative of the medium to be examined.

It is therefore an object of the invention to provide a sampling apparatus and a sampling method whereby the desired sample volume can be changed in a simple manner without mechanical intervention even during operation, with any accumulation of solids in the sample contained in the dosing vessel being avoided, so that a sample representative of the medium is obtained.

To attain this object, the invention provides an apparatus for taking a predetermined volume of a sample of a medium flowing in an open channel or by gravity through a pipe, said apparatus comprising:

a control unit;

a pneumatic control gear controlled by the control unit;

a pump switched by the control unit;

a sample collecting vessel for receiving the sample volume;

a drain device;

a hose or tube used as a suction line, through which the sample is conveyed via an inlet into the sample collecting vessel; and a detection unit incorporated in the suction line which determines the presence of the medium in the suction line.

To attain the above object, the invention further provides a method of taking a predetermined volume of a sample of a medium flowing in an open channel or by gravity through a pipe, comprising the following steps:

A control unit switches a pump, which is pneumatically connected with a sample collecting vessel, and at least one valve in a pneumatic control gear comprising different valves in such a manner that a partial vacuum is created in the sample collecting vessel;

through the partial vacuum, the medium is drawn from the channel through the suction line into the sample collecting vessel;

as soon as a detection unit incorporated in the suction line determines a presence of the medium and signals this to the control unit, a preselectable time corresponding to a desired volume of the sample and monitored by the control unit begins to run;

after expiration of the time, the control unit turns the pump off and switches the pneumatic control gear so that the sample collecting vessel is opened to the atmosphere;

under the action of gravity, the medium still contained in the suction line and not needed for the sample flows back into the channel; and the sample in the sample collecting vessel is drained off into at least one sample container.

In a preferred embodiment of the apparatus according to the invention, the drain device comprises a flexible hose and a squeezing device for squeezing off the hose.

In another preferred embodiment of the apparatus according to the invention, the detection unit is located as close to the inlet of the sample collecting vessel as possible.

In a further preferred embodiment of the apparatus according to the invention, the detection unit comprises an optical, capacitive, or inductive sensor or a conductivity sensor for determining the presence of the medium as well as a signal generator connected to the sensor and providing a signal indicating the presence of the medium to the control unit.

In a further preferred embodiment of the apparatus according to the invention, the pneumatic control gear is a valve block with a camshaft gear or with solenoid valves.

In still another preferred embodiment of the apparatus according to the invention, the sample collecting vessel has, in the area of its inlet, an emergency switch which stops the supply of the medium to the sample collecting vessel.

In a preferred embodiment of the method according to the invention, the time required to draw the medium into, and collect it in, the sample collecting vessel is determined for at least one predetermined sample volume, so that times associated with different sample volumes can be determined, and the time determined for at least one desired sample volume is entered into and/or stored in the control unit.

In another preferred embodiment of the method according to the invention, a time corresponding to a desired sample volume and stored in the control unit is used to control the pump during the sampling operation.

In a further preferred embodiment of the method according to the invention, prior to a new sampling operation, the suction line is blown by the pump with compressed air.

One particular advantage of the invention is that only a quantity of the medium corresponding to the desired sample volume is conducted into the sample collecting vessel. As a result, the solids content of the sample finally drained off into the sample container is identical with the solids content of the medium in the channel or pipe. An additional step for dosing the sample volume to be drained off is not necessary.

Another particular advantage of the invention is that it allows the desired sample volume to be adjusted without the need to shorten or rotate the dosing tube extending into the sample collecting vessel or without the need for any other mechanical intervention in the sampling apparatus. Simply by changing the time predetermined for the sampling, it is possible to adjust a sample volume proportional to the flow rate of the medium in the channel or pipe. Since, in addition, the time controlling the sampling is managed in the control unit and can be stored there, it is possible to automatically adapt the duration of inflow of the medium into the sample collecting vessel, and thus the sample volume, to a measured flow-rate value of the medium in the channel or pipe.

The invention will become more apparent from the following description of a preferred embodiment taken in conjunction with the accompanying drawing.

The single FIGURE of the drawing is a schematic representation of a sampling apparatus 10, which includes a control unit 12, for example a programmable control unit, which can operate valves of a pneumatic control gear 16 via an electric first line 14 and switch an electrical pump 20 via an electric second line 18. The pump 20 is preferably a vacuum diaphragm pump. Various control units can be used for the invention, for example a control unit 12 which initiates and controls the sampling fully automatically, but initiation by a user is also possible. Without departing from the scope of the invention, use can also be made of a semiautomatic control unit 12 which, after initiation of a sampling operation by a user, controls the further sequence of steps of the sampling process.

For the pneumatic control gear 16, a valve block with step control, preferably with a cam controller, is particularly suitable. Such cam controllers have the advantage of being not susceptible to corrosion, since a diaphragm separates moving parts from paths through which air flows. A cam controller particularly suited for the invention is available from Endress+Haussner Wetzer GmbH+Co. KG, D-87481 Nesselwang, under the designation "AIR-MANAGER". It is also possible, however, to use a valve block with conventional solenoid valves for the pneumatic control gear.

The pneumatic control gear 16 controlled by the control unit 12 is incorporated in a first tube 22, which connects the pump 20 with a sample collecting vessel 24. The sample collecting vessel 24, which receives the sample volume, is closed at the bottom by a drain device 26. The latter comprises, for example, a flexible hose 28, through which the sample contained in the sample collecting vessel 24 can be drained off into at least one sample container 32. The hose 28 is closed using a squeezing device 30, preferably a pneumatic pinch cock with a roller diaphragm. A pneumatic pinch cock particularly suited for the invention is available from Endress+Hauser Wetzer GmbH+Co. KG, D-87481 Nesselwang.

A suction line 34, for example a hose line or tube, connects the medium 36 flowing in an open channel 38 with the sample collecting vessel 24. Instead of extending into the open channel, the suction line 34 may end in a pipe through which the medium flows by gravity.

An opening in a lid 39 of the sample collecting vessel 24, which opening contains the end of the suction line 34 extending from above into the sample collecting vessel 24, will be referred to as an inlet 40. Near this inlet 40, the suction line 34 incorporates a detection unit 42 which signals the presence of the medium 36 over an electric third line 44 to the control unit 12. To this end, the detection unit 42 preferably comprises a sensor determining the presence of the medium 36 drawn in, for example an optical, capacitive, or inductive sensor or a conductivity sensor, as well as a signal generator which provides a signal to the control unit 12.

An emergency switch 46 provided on the inside of the lid 39 of the sample collecting vessel 24 signals to the control unit 12 over an electric fourth line 48 when it is reached by the medium 36 accumulating in the sample collecting vessel 24. The further flow of medium 36 into the sample collecting vessel 24 will then be cut off to prevent the sample collecting vessel 24 from overflowing.

Electric power sources for supplying the electrical devices provided in the sampling apparatus 10, and the electric supply lines necessary therefor, do not form part of the invention. They are familiar to those skilled in the art and are not shown in order to simplify the illustration.

Prior to the sampling proper, the time required to draw the medium into and collect it in the sample collecting vessel is determined for at least one predetermined sample volume. Next, times associated with different sample volumes are determined and are entered into and/or stored in the control unit, either in the form of a table or in the form of a corresponding functional interrelationship. The respective time for a desired sample volume is then retrieved from or selected and set in the control unit.

The sampling proper is initiated either by a user if the control unit 12 is a semiautomatic unit, or by the control unit 12 in accordance with a predetermined program run if the apparatus is fully automatic. The control unit 12 switches the pneumatic control gear 16, particularly at least one of the valves of the pneumatic control gear 14, via the electric first line 14 and the pump 20 via the electric second line 18 in such a way that the sample collecting vessel 24 is evacuated via the first tube 22, a pneumatic line. The drain device 26 is closed.

Through the partial vacuum in the sample collecting vessel 24, the medium 36 flowing in the open channel 38 or through the pipe is drawn through the suction line 34 connected with the sample collecting vessel 24 into the sample collecting vessel 24. When the medium 36 passes the detection unit 42, the sensor of the latter triggers and signals the presence of the medium 36 to the control unit 12. The control unit 12 monitors the expiration of a preselected time period which corresponds to the desired sample volume of the medium, and during which the medium 36 flows into the sample collecting vessel 24.

When the time corresponding to the desired sample volume has elapsed, the control unit 12 switches off the pump 20 and the pneumatic control gear 16, particularly one of the valves therein, so that the (under)pressure prevailing in the sample collecting vessel 24 until then is compensated to the atmosphere. Under the action of gravity, the medium 36 still contained in the suction line 34 then flows back into the open channel 38. The sample collecting vessel 24 contains no excess medium, but exclusively the desired sample volume, so that additional dosing of the sample as is required in conventional samplers is no longer necessary. No excess medium need be pressed out of the sample collecting vessel 24 back into the channel 38. Thus, in the case of solids-containing media, the invention prevents solids in the excess volume of the medium from sedimenting in the sample collecting vessel 24 and thus falsifying the solids concentration of the sample proper.

After the sampling operation and the venting of the sampling apparatus 10, a sample container 32 is placed below the drain device 26, unless it is already present there. The squeezing device 30 is now opened and the sample volume drained off. If the volume of the medium in the sample collecting vessel 24 is sufficient, two or more, possibly smaller, sample containers can be filled.

Particularly in the case of heavily sedimenting media, it has turned out that it may be necessary to blow the suction line 34 after a sampling operation and prior to a new sampling operation in order to prevent sedimented solids from depositing in the suction line 34 and adulterating a subsequent sample. After each sampling operation, the suction line 34 can be cleared of deposited solids with compressed air from the pump 20.

In the invention, conventional dosing vessels as described by way of introduction can be used for the sample collecting vessel 24. The sensor switch mounted in the sample collecting vessel 24, which stops the drawing in of the medium, can then be used as the emergency switch 46, so that overflowing of the sample collecting vessel 24—for whatever reason—is prevented. To this end, the sensor switch is either connected to the control unit 12, which then turns off the pump 20 in the event of overflow, or inserted as a circuit breaker directly into an electric supply line for the pump 20.

What is claimed is:

1. An apparatus for taking a predetermined volume of a sample of a liquid, said apparatus comprising:

a sample collecting vessel for receiving the sample;

a suction line through which the sample is conveyed via an inlet into the sample collecting vessel;

a drain device for draining off the sample into a sample container;

a control unit;

a pump switched by the control unit, the pump being operable to evacuate the sample collecting vessel and the suction line for drawing the sample into the suction line;

a control gear controlled by the control unit, the control gear being operable to pneumatically interconnect the pump with the sample collecting vessel; and a detection unit being operable
      to signal a presence of liquid in the suction line, and
      to trigger the control unit for monitoring a preselected time period corresponding to said predetermined volume of the sample, wherein air for venting the sample collecting vessel and said suction line is conveyed via the control gear into the sample collecting vessel after the preselected time period has elapsed.

2. An apparatus as claimed in claim 1 wherein the drain device comprises a flexible hose and a squeezing device for squeezing off the hose.

3. An apparatus as claimed in claim 1 wherein the detection unit is located as close to the inlet of the sample collecting vessel as possible.

4. An apparatus as claimed in claim 1 wherein the detection unit comprises an optical, capacitive, or inductive sensor or a conductivity sensor for determining the presence of liquid, and a signal generator connected to the sensor and providing a signal indicating the presence of liquid to the control unit.

5. An apparatus as claimed in claim 1 wherein the pneumatic control gear is a valve block with a camshaft gear or with solenoid valves.

6. An apparatus as claimed in claim 1 wherein the sample collecting vessel has, in the area of its inlet, an emergency switch which stops the supply of the medium to the sample collecting vessel.

7. A method for taking a predetermined volume of a sample of a liquid, said method comprising the following steps:

interconnecting a sample collecting vessel via a suction line with the liquid;

interconnecting a pump with the sample collecting vessel pneumatically;

drawing the sample via the suction line by a vacuum in the sample collecting vessel generated with the pump;

detecting a presence of liquid drawn in the suction line and triggering a control unit for monitoring an expiration of a preselected time period corresponding to the predetermined volume of the sample;

conveying the sample into the sample collecting vessel via the suction line;

venting the sample collecting vessel after the preselected time period corresponding to the predetermined volume of the sample has elapsed; and draining off the sample into at least one sample container.

8. A method as claimed in claim 7, further comprising the steps of:

determining, prior to the drawing step, time required to draw the sample into and collect the sample in the sample collecting vessel for at least one predetermined sample volume, so that times associated with different sample volumes can be determined, and storing the times determined for at least one desired sample volume in the control unit.

9. A method as claimed in claim 8, further comprising the steps of:

setting the preselected time period, for control of the pump during the drawing step, to the time corresponding to the predetermined volume of the sample already stored in the control unit.

10. A method as claimed in claim 7, further comprising the step of:

blowing, prior to a new sampling operation, the suction line with compressed air from the pump.

* * * * *

UNITED STATES PATENT AND TRADEMARK OFFICE
CERTIFICATE OF CORRECTION

PATENT NO. : 6,453,759 B1
DATED : September 24, 2002
INVENTOR(S) : Hubert Lebski, Dieter Waldhauser, Wilhelm Schneider and Helmut Einsiedler It is certified that error appears in the above-identified patent and that said Letters Patent is hereby corrected as shown below:

<u>Title page,</u>
Item [73], please add the following Assignee:
-- [73] Assignee: Endress + Hauser Wetzer GmbH + Co. KG, Nesselwang, (DE) --.

Item [56], References Cited, FOREIGN PATENT DOCUMENTS, please add the following:
-- DE        29514872        12/21/95 --.

Signed and Sealed this

Twenty-fourth Day of December, 2002

JAMES E. ROGAN
*Director of the United States Patent and Trademark Office*